US012702359B2

(12) United States Patent
David et al.

(10) Patent No.: US 12,702,359 B2
(45) Date of Patent: Aug. 11, 2026

(54) MEDICAL PATCH

(71) Applicant: Given Imaging LTD., Yoqneam (IL)

(72) Inventors: Eyal David, Atlit (IL); Eli Ziv, Karmiel (IL); Yaniv Birnboim, Shaarey Tiqwa (IL); Avishag Spillinger, Kiriat Haim (IL); Vitaly Fastovsky, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 710 days.

(21) Appl. No.: 17/920,429

(22) PCT Filed: May 20, 2021

(86) PCT No.: PCT/IL2021/050583

§ 371 (c)(1),
(2) Date: Oct. 21, 2022

(87) PCT Pub. No.: WO2021/234706

PCT Pub. Date: Nov. 25, 2021

(65) Prior Publication Data

US 2023/0157638 A1 May 25, 2023

Related U.S. Application Data

(60) Provisional application No. 63/028,920, filed on May 22, 2020.

(51) Int. Cl.
*A61B 5/00* (2006.01)
*A61B 5/07* (2006.01)

(52) U.S. Cl.
CPC ........ *A61B 5/68335* (2017.08); *A61B 5/0022* (2013.01); *A61B 5/073* (2013.01); *A61B 5/6861* (2013.01); *A61B 2562/12* (2013.01)

(58) Field of Classification Search
CPC ........... A61B 2562/12; A61B 2562/14; A61B 2562/16; A61B 2562/242; A61B 5/0002;
(Continued)

(56) References Cited

U.S. PATENT DOCUMENTS

| | | |
|---|---|---|
| 7,004,917 B2 | 2/2006 | Henderson et al. |
| D608,007 S | 1/2010 | Arbesman et al. |

(Continued)

FOREIGN PATENT DOCUMENTS

| | | |
|---|---|---|
| CN | 105050490 A | 11/2015 |
| CN | 109923419 A | 6/2019 |

(Continued)

OTHER PUBLICATIONS

International Search Report and Written Opinion of the International Searching Authority issued in corresponding application PCT/IL2021/050583 mailed Oct. 25, 2021 (21 pages).

(Continued)

*Primary Examiner* — Scott Luan
(74) *Attorney, Agent, or Firm* — Carter, DeLuca & Farrell, LLP

(57) ABSTRACT

A medical patch configured for being applied to a patient and for communicating with an in-vivo device located within the patient's body; The medical patch comprises an adhesive surface configured for adhering the patch to the patient's skin; and a communication arrangement configured for providing communication between the medical patch and the in-vivo device.

17 Claims, 4 Drawing Sheets

(58) Field of Classification Search
CPC ... A61B 5/0022; A61B 5/073; A61B 5/68335; A61B 5/6843; A61B 5/6844; A61B 5/6861
See application file for complete search history.

(56) References Cited

U.S. PATENT DOCUMENTS

| | | | |
|---|---|---|---|
| D877,306 S | 3/2020 | Liu | |
| D980,055 S | 3/2023 | Konstenius | |
| D1,068,084 S | 3/2025 | Fu | |
| D1,073,084 S | 4/2025 | Karvandi | |
| D1,093,626 S | 9/2025 | Yuan | |
| D1,094,727 S | 9/2025 | Hagerty et al. | |
| D1,100,247 S | 10/2025 | Ou et al. | |
| D1,103,807 S | 12/2025 | Hayman et al. | |
| 12,521,021 B2 | 1/2026 | Telfort et al. | |
| 2014/0206977 A1 | 7/2014 | Bahney et al. | |
| 2014/0343378 A1 | 11/2014 | Arneson et al. | |
| 2014/0378799 A1* | 12/2014 | Chattaraj | B32B 7/12 600/300 |
| 2017/0238872 A1 | 8/2017 | Donnay et al. | |
| 2019/0246928 A1 | 8/2019 | Bahney et al. | |

FOREIGN PATENT DOCUMENTS

| | | | |
|---|---|---|---|
| EP | 2091424 | B1 | 8/2009 |
| EP | 2471439 | B1 | 5/2013 |
| EP | 3586732 | A1 | 1/2020 |
| JP | D20174672 | | 12/2017 |
| WO | 2012125425 | A2 | 9/2012 |
| WO | 2014116825 | A1 | 7/2014 |
| WO | 2014165071 | A1 | 10/2014 |
| WO | 2016108888 | A1 | 7/2016 |
| WO | 2018119193 | A1 | 6/2018 |
| WO | 2019241676 | * | 12/2019 |
| WO | 2019241676 | A1 | 12/2019 |

OTHER PUBLICATIONS

Office Action issued in Japanese Application No. 2022-571257 mailed Jan. 28, 2025, together with English language translation (11 pages).

Office Action issued in corresponding application CN202180037194.2 dated Jun. 12, 2025, together with English language translation retrieved from the Global Dossier.

Chinese Office Action issued in corresponding Chinese Application No. 202180037194.0 dated Sep. 1, 2025, together with English language translation retrieved from the Global Dossier, 17 pages.

European Examination Report issued in corresponding application EP 21740240.3 dated Jul. 15, 2025.

Notice of Allowance issued in related U.S. Appl. No. 29/951,064 mailed Apr. 24, 2026, 9 pages.

* cited by examiner

MEDICAL PATCH

CROSS-REFERENCE TO RELATED APPLICATIONS

This application is a U.S. National Stage Application filed under 35 U.S.C. § 371(a) of International Patent Application No. PCT/IL2021/050583, filed on May 20, 2021, which claims the benefit of the filing date of provisional U.S. Patent Application No. 63/028,920, filed on May 22, 2020.

TECHNOLOGICAL FIELD

The present invention is in the field of medical patches, in particular, medical patches configured for communicating with in-vivo devices.

BACKGROUND OF THE INVENTION

Medical patches (sometimes referred to as stick to skin solutions, skin patches and medical wearable devices) are devices configured for being applied to a patient's skin for one of two main purposes: medicative and monitoring.

Medicative patches may be configured for affecting the patient in various ways in order to improve or sustain their medical condition. One common example is transdermal patches comprising a medication and configured for providing the medication to the patient via the skin, either by puncturing the skin (with a needle) or by transdermal diffusion. Another example is therapeutic patches such as a head patch configured for treating Glioblastoma in patients by generating tumor treating field (TTFields).

Monitoring patches, one the other hand, are configured for gathering information about the patient either by directly sensing different parameters of the patient (e.g. micro-movements, electricity, pulse etc.) or for communicating with a device configured for sensing such parameters. One example may be a patch configured for communicating with an implanted pacemaker.

Medical patches may be applied to the skin in various ways, inter alia, by adhesion.

Acknowledgement of the above references herein is not to be inferred as meaning that these are in any way relevant to the patentability of the presently disclosed subject matter.

GENERAL DESCRIPTION

In accordance with a general aspect of the subject matter of the present application there is provided a medical patch configured for being applied to a patient and for communicating with an in-vivo device located within the patient's body, said medical patch comprising:

- an adhesive surface configured for adhering the patch to the patient's skin; and
- a communication arrangement configured for providing communication between the medical patch and the in-vivo device.

The in-vivo device of the present application may be an in-vivo device configured for movement within the patient's body during operation. In accordance with a specific example, the in-vivo device may be a swallowable in-vivo device configured for traveling along at least a portion of the patient's GI tract, e.g. a swallowable capsule, an endoscope, an esophageal catheter etc.

The medical patch may comprise an adhesive film having an inner surface and an outer surface, at least a portion of said inner surface constituting the adhesive surface. The adhesive layer may further comprise:

- a removable protective liner arrangement attached to the inner surface and configured for protecting it before application of the patch; and
- a removable support liner arrangement configured for providing the adhesive film with structural integrity during the process of application.

Both the protective liner and support liner are configured for being removed from the adhesive film during application thereof to the patient.

The adhesive film may comprise a central region and a peripheral region extending around the central region. The peripheral region of the adhesive film may extend partially around the central region, such that part of an outer edge of the adhesive film is constituted by a portion of the central region. In accordance with a particular example, the peripheral region may fully extend around the central region, such that the entire outer edge of the adhesive film is constituted by a portion of the peripheral region.

In order to increase comfort to the patient, the adhesive film is chosen to be as thin and as flexible as possible, allowing it to conform to the patient's skin and movements. In accordance with a particular example, the thickness of the adhesive film may be in the range of 0.05 mm to 0.5 mm, more particularly, in the range of 0.1 mm to 0.4 mm, and even more particularly, in the range of 0.12 mm to 0.2 mm.

However, the low thickness of the adhesive film also affects its structural integrity, to a degree making it nearly impossible to properly place and adhere the adhesive film to the patient, on its own. The support liner arrangement, on the other hand, may be substantially thick and rigid enough to provide the required structural integrity, allowing the patient or a healthcare practitioner to properly adhere the adhesive film to the patient's body.

The medical patch is designed such that the functional components of the medical patch also provide the required structural integrity to the central region of the adhesive film, while the support liner pieces provide the required structural integrity to the peripheral region of the adhesive film.

In general, the medical patch is applied in several sequential steps:

- gradual removal of the protective liner arrangement while placing the adhesive layer against the patient's skin;
- gradual removal of the support liner arrangement; and
- pressing on the adhesive film to reinforce adherence.

The medical patch of the present application is configured for being placed against the patient's body, in a predetermined location, such that the entire surface of the adhesive film adheres to the patient's skin. Since the patch is configured for providing communication with the in-vivo device, proper placement and location of the patch directly affect the quality of communication with the in-vivo device.

The protective liner arrangement may comprise a protective liner piece configured to cover the adhesive side. The liner arrangement may also comprise more than one protective liner protective piece, wherein the arrangement of the protective liner pieces may also dictate the order of removal thereof from the inner surface. In accordance with a particular example, the protective liner arrangement may comprise a middle protective liner piece and two side protective liner pieces (also referred herein as wing pieces), one on either side of the central protective liner piece. It should be understood that 'middle' is used herein simply to denote a piece between the two outer pieces, and is not limited to a geometric middle.

In operation, the middle protective liner piece may be peeled away from the inner surface of the adhesive film first, whereafter the patch may be placed against the patient's skin, allowing proper alignment and adhesion to the patient's skin, performed either by a medical practitioner or the patient themselves. During this step, the portions of the adhesive film covered by the wing pieces may facilitate convenient gripping of the patch by the person applying the patch. After the middle protective liner piece has been adhered to the patient, each of the wing pieces may be peeled away and adhered to the patient, thereby allowing proper adhesion of the entire patch.

Once the patch is properly adhered to the patient's body, the support liner pieces may be removed from the outer surface of the adhesive film, leaving a peripheral portion of the adhesive film free of any additional layers. As in the case of the protective liner arrangement, the support liner arrangement may also dictate the order of removal of support liner pieces from the adhesive film.

The support liner pieces may also be designed to have tabs or pulling extensions allowing more convenient separation of the protective liner from the adhesive layer when attempting to peel it away therefrom. One advantage of such a design is preventing accidental peeling of the adhesive layer from the skin when attempting to separate the liner piece from the adhesive layer. In addition, The tabs may also be configured to be angled with respect to the plane of the patch, thereby protruding outwards, away from the skin, thereby being more clearly visible during self application of the patch, especially for people with a larger abdominal area, which would naturally obscure the visibility of the patch. The tabs may also be numbered, indicating to the person applying the patch the order in which the support liner pieces should be peeled off.

Since the medical patch is required for being properly located on the patient's skin in order to maintain proper communication with the in-vivo device, and since the adhesive film is extremely thin, it is required that removal of the support liner pieces does not cause improper distortion of the adhesive layer, detachment thereof, undesirable tugging forces during removal and/or any discomfort to the patient. It should also be noted that the arrangement is such that the adherence force between the support liner pieces and the adhesive layer is weaker compared to the adhesion force between the adhesive layer and the patient's skin, whereby removal of the support liner piece is less likely to peel off the adhesive layer from the patient's skin.

Finally, after the support liner pieces had been removed, the adhesive film may be further manually smoothed and/or pressed against the patient's skin to provide optimal adhesion.

In accordance with one aspect of the subject matter of the present application there is provided a medical patch configured for being applied to a patient and for communicating with an in-vivo device located within the patient's body, said medical patch comprising:

- an adhesive film having an inner surface and an outer surface, at least a portion of said inner surface being configured for adhesion to the patient, when the patch is applied, said film having a central region and a peripheral region; and
- a support liner arrangement coupled to the outer surface of the adhesive film along a portion of at least the peripheral region thereof, and configured for:
  - a) providing the adhesive film with structural integrity during application of the patch; and
  - b) being removed from the adhesive film after said application;
- wherein the support liner arrangement comprises two or more support liner pieces, the majority of each of the support liner pieces covering an individual portion of the peripheral region, and wherein the shape and size of the support liner pieces is designed to reduce tugging forces applied to the adhesive film during removal of the support liner pieces.

The medical patch may have a generally prolonged shape, having a length dimension greater than its width dimension. In particular, the shape may resemble a curved rectangle, a rounded edged rectangle or a banana-shaped. For the purpose of this application, the term 'side portion' refers to the portion of the rectangle containing the corners of the rectangle and covered by the wing pieces of protective liner arrangement, and the term 'middle portion' refers to the portion located between the side portions, and covered by the middle protective liner piece. It should be noted that the term 'corners' is not limited to sharp corners.

Therefore, as suggested by the novel concept of the present application, the support liner arrangement is divided into several individual support liner pieces, each covering a different sector of the peripheral region. In particular, the arrangement, shape and size of the support liner pieces is chosen such that removal thereof from the outer surface of the patch may be performed from the middle outwards. Specifically, the design is such that during removal of any of the support liner pieces, the adhesive film is not being tugged towards the middle.

Each support liner piece may have a prolonged shape extending along a sector of the peripheral portion of the outer surface of the adhesive film. Each support liner pieces extends between a lead end located closer to the middle of the patch and a tail end located closer to a extremity of the patch, along a centerline (also referred herein as a median line). The design of the support liner pieces is such that the trajectory of the centerline does not curve over a certain angle such that. In particular, when a support liner piece is removed from the outer surface of the adhesive layer, from the middle outwards, it does not curve back towards the middle.

Thus, the centerline of each support liner piece does not extend along a portion of the peripheral region constituting a turn angle smaller than roughly 100°. The turn angle is defined herein as an internal angle measured between a first tangent to the centerline at the lead point thereof and a second tangent to the centerline at an endpoint thereof.

It has been discovered that sectoring the peripheral region of the adhesive film in the above mentioned manner allows reducing the tugging forces acting on the adhesive film during application.

In addition to the above, the shape and size of the support liner pieces is chosen such that the area covered by each of the support liner pieces is generally similar so as not to create an imbalance in the tugging forces between different support liner pieces. Thus, for example, one support liner piece may be longer and thinner, while another support liner piece may be shorter and thicker.

In accordance with a particular example, the support liner arrangement may comprise four support liner pieces, two support liner pieces extending around a top edge of the peripheral region (correlating with a first long edge of the rectangle), and two support liner pieces extending along a bottom curved edge of the peripheral region.

The peripheral region is not required to have a uniform width around the central region, and according to a particular example, a top portion of the peripheral region may be substantially wider than the bottom portion thereof.

In accordance with a further example, the support liner arrangement may be divided into five, six, seven or eight different pieces, each covering a different sector of the peripheral region.

It should be appreciated that segmenting the peripheral portion as suggested above requires a certain trade-off—increasing the number of support liner pieces in order to reduce undesirable tugging effects increases the complexity of the application process and vise versa—reducing the number of support liner pieces for simplifying the application process increases undesirable tugging effects.

In accordance with another aspect of the subject matter of the present application there is provided a method for fitting a medical patch of the previous aspect of the present application to a patient's body, said method comprising:

a) removing a protective liner piece from the inner surface of the adhesive layer of the patch and applying the exposed portion of the inner surface to the patient;
b) repeating step (a) until all protective liner pieces have been removed and the inner surface is fully applied to the patient:
c) removing a support liner piece from the outer surface of the adhesive layer from the middle outwards; and
d) repeating step (c) until all support liner pieces have been removed and the peripheral portion of the outer surface is exposed.

The method may further comprise an additional step (e) of pressing on the peripheral portion of the outer surface for reinforcing adhesion of the film layer to the patient.

In accordance with another aspect of the subject matter of the present application there is provided a medical patch configured for being applied to a patient and for communicating with an in-vivo device located within the patient's body, said patch comprising:

a communication layer comprising a communication arrangement configured for providing communication between at least (a) the in-vivo device and the medical patch, and (b) between the medical patch and an external device;

an adhesive film configured for coming into contact with the patient for the purpose of application of the medical patch;

a spacing layer interposed between the adhesive layer and the communication layer and configured for reducing deformational changes on the communication layer, caused by deformations to the patient's skin surface, as well as maintaining a proper transmission performance; and one or more constructive adhesive layers interposed between the communication layer, the adhesive film and the spacing layer, and configured for attachment of said layers to one another.

The communication layer may comprise communication components such as antennas, receivers, modems, switching components etc. The communication layer may be in the form of a printed antenna, having all communication components embedded within the printed layer.

The adhesive film may be essentially similar to the adhesive film described in connection with the previous aspect of the present application, being essentially thin and including a central region and a peripheral region.

The spacing layer may be made of a material having a thickness chosen to be such that minimally interferes with transmission and reception of signals between the communication layer and the in-vivo device. In addition, the material may be chosen such that it is configured to maintain its shape and/or return to its original shape following deformation, thereby guaranteeing maintaining a uniform distance between the communication layer and the skin layer. One example of such a material may be a closed-cell foam material.

In particular, the spacing layer may have a combination of three or more of the following features:

low water retention (or low water absorption)—reducing the amount of water retained in the foam layer;

puncture resistance—reducing the risk of accidental puncture of the medical patch by the user;

differential stretchability—reducing the risk of tear of the medical patch;

low breathability—reducing the chances of vapor reaching the functional components of the medical patch;

good bond strength—increasing proper adhesion to the rest of the layers of the medical patch;

low electric loss constant—reducing interference with communication; and high elastic recovery—increasing the chances of the medical patch properly withstanding stretching caused by movement and position of the patient.

Following extensive testing, some such materials have been found, for example, and EVA foam by 3M (3M EVA MSX-7373A).

It should also be noted here that most medical patches required breathability in order to better deal with sweating issues by the patient by allowing sweat to vaporize through the patch. However, in the present invention, such breathability proves disadvantageous, since such vapor may affect transmission between medical patch and the in-vivo device, by changing the spacing and/or medium through which communication is transmitted.

The adhesive layers may be double-sided adhesive layers, allowing attachment of layers on either side of the adhesive layer. Alternatively, the adhesive layer may be a transfer adhesive layer, i.e. an adhesive held by a mesh. The adhesive layers may be formed with cutouts, shaped, sized and located to receive therethrough components protruding from any of the layers.

The medical patch may further comprise:

at least one processing unit configured for being attached to the communication layer for receiving, processing and sending signals to and from the communication layer; and at least one power source coupled to the processor and the communication layer and configured for providing power thereto.

The medical patch may further comprise a cover layer configured for covering the external portion of the medical patch. In particular, the cover layer may comprise cavities configured for housing at least the power source and the processing unit.

In accordance with a particular example, the medical patch may comprise the following order of layers:

the adhesive film comprising a central region and a peripheral region, the adhesive film having an adhesive side and a non-adhesive side;

a support liner arrangement fitted to the peripheral region of the adhesive film;

a first adhesive layer fitted to the central region of the adhesive film;

the spacing layer;

a second adhesive layer;

the communication layer;

the power source and processing unit fitted to the communication layer;

a third adhesive layer placed over the communication layer with a cutout accommodating the power source and processing unit; and the cover layer.

The cover layer, functioning as the external layer of the patch (farthest from the patient), may be flexible for maximum, comfort. However, since the communication layer comprises rigid components which may need protection, at least the processing unit may be covered by a rigid cage.

The processing unit may also comprise one or more light sources used for indicating events and issuing alerts to the patient, and the cage may be complementarily designed to have at least one cut out and/or transparent window aligned with the one or more light sources, allowing visibility through the cage.

In addition, the processing unit may comprise one or more USB ports and the cage may be complementarily designed to have at least one cut outs configured for allowing access to the one or more USB ports. The cut outs may be provided with a flap or pre-designed cut-out which is intended to be generally closed, and may be removed/opened if access to a USB port is required. The cage is further designed such that the flap may be closed again after it opening.

In accordance with still another aspect of the subject matter of the present application there is provided a medical patch configured for being applied to a patient and for communicating with an in-vivo device located within the patient's body, said patch comprising:

a functional portion;

a contact portion; and a spacing layer made of a non-porous material as described in the previous aspect of the subject matter of the present application.

In accordance with another aspect of the subject matter of the present application, there is provided a casing configured for containing a medical patch of the above aspects of the subject matter of the present application and a swallowable in-vivo device configured for being in communication with the medical patch, wherein said casing comprises a first safety arrangement configured for preventing the patch from spontaneously commencing operation, and a compartment configured for accommodating the in-vivo device, said compartment comprising a second safety arrangement configured for preventing the in-vivo device from spontaneously commencing operation.

In accordance with still a further aspect of the subject matter of the present application, there is provided a kit comprising a casing accommodating therein a medical patch of the previous aspects of the present application, and a swallowable in-vivo device, wherein said patch and said in-vivo device are already pre-paired with one another before being removed from the casing.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

Figures 1A, 1B, 1C:
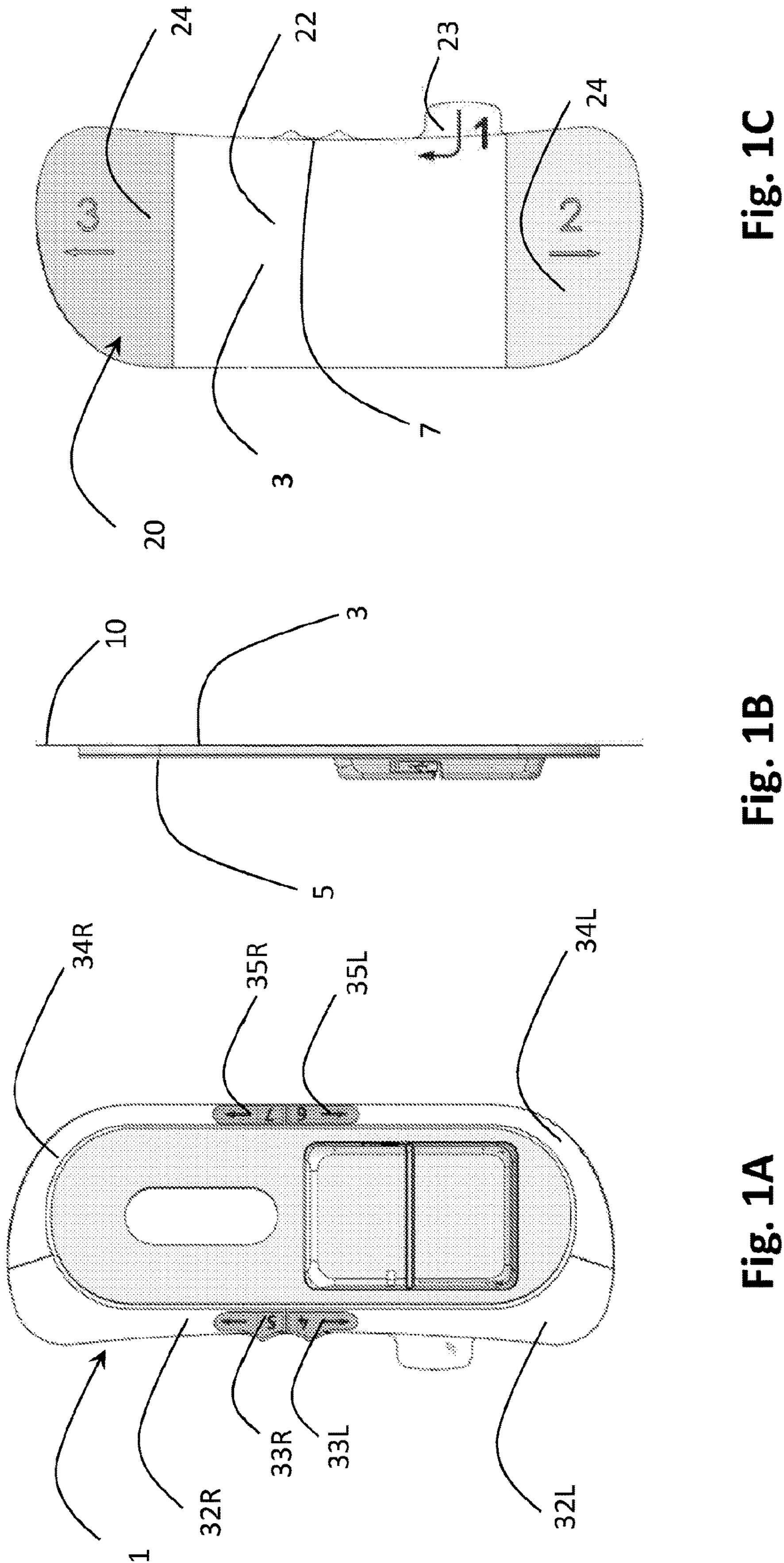
FIGS. 1A, 1B and 1C are a schematic front, side and rear views of a patch in accordance with the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF EMBODIMENTS

Attention is first drawn to FIG. 1, in which a wearable medical patch (hereinafter: patch) is shown, generally designated 1, and configured for being adhered to a patient's skin. The patch 1 has a contact side 3, also referred herein as an inner face, configured for coming in contact with the patient's skin, when the patch 1 is applied, and an outer face 5 configured for facing away from the patient, when the patch 1 is applied.

The patch 1 further comprises a communication arrangement CA (shown in FIG. 2) configured for performing at least one of the following:

receiving signals from an in-vivo device configured for being inserted into the patient's body;

sending signals to the in-vivo device; and transmitting data from the patch 1 to an external source (e.g. phone, tablet, cloud etc.).

The patch 1 comprises an adhesive film 10 configured for adhering to the patient's skin when the patch 1 is applied. The adhesive film 10 is relatively thin and has a nominal thickness ranging between 0.05-0.3 mm. In order to protect the adhesive side 12 of the adhesive film 10, the adhesive film 10 is fitted with a protective liner arrangement 20, comprising a middle protective liner piece 22 (bearing the indicia 1) and two side protective liner pieces 24 (each bearing the indicia 2). The protective liner pieces 22, 24 are configured for protecting the adhesive surface 12 of the adhesive film 10 when in storage and prior to application of the patch 1.

Each of the protective liner pieces 22, 24, has a pulling tab, 23, 25 respectively, configured for allowing convenient removal of the protective liner pieces 22, 24. In addition, the indicia on the tabs 23, 25, dictates the order of removal of the protective liner pieces 22, 24, when applying the patch 1.

Since the adhesive film 10 is extremely thin, and since the protective liner pieces 22, 24, are to be removed before application of the patch 1, the adhesive film 10 requires and additional reinforcing layer allowing it to maintain structural integrity during application of the patch 1. For this purpose, the adhesive film 10 is also provided with a supportive liner arrangement 30 comprising four support liner pieces 32L, 32R, 34L and 34R.

In operation, when the patch 1 is applied to the patient, the middle protective liner piece 22 is first removed by pulling on the tab 23, and the patch 1 is then applied to the patient such that the adhesive portion of the adhesive film 10 revealed by the removal of the middle protective liner piece 22.

Figure 3A:
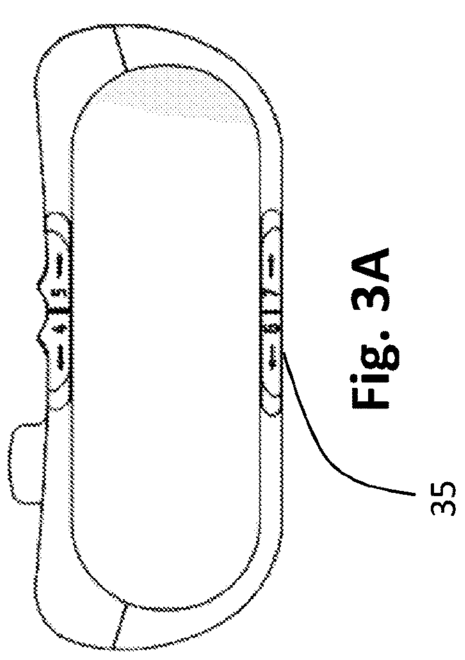
FIGS. 3A and 3B are schematic top and side views of a tab arrangement of the patch under another example of the present application.
Figure 3B:
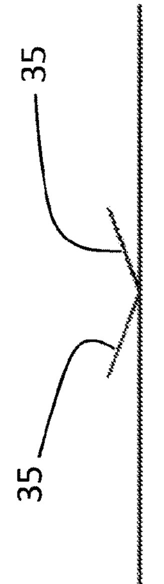

With additional reference being made to FIGS. 3A and 3B, the tabs 35 are configured for being angled to the plane of the patch 1 and have a greater area, making it more convenient for the person applying the patch to remove the support liner piece from the patch 1, once it has been adhered to the body.

In order to increase the accuracy of placement, the patch 1 is provided with a placement indent 7, configured for being aligned with the area under the naval. This further allows preventing the patch from being applied at an angle or even upside down.

Once the middle portion of the adhesive film 10 is adhered to the patient, the two side protective liner pieces 24 are removed by pulling on the tabs 25, in and outwards direction, while applying pressure to the supportive liner arrangement 30 in order to assure proper adhesion to the patient's skin.

Once the entire adhesive surface 12 of the adhesive film 10 is adhered to the patient's skin, the protective liner pieces 32L, 32R, 34L and 34R are to be removed, sequentially, leaving only the thin adhesive film 10 around the periphery of the patch 1.

It is noted that each of the protective liner pieces 32L, 32R, 34L and 34R also has a pulling tab 33L, 33R, 35L and 35R respectively, and are also marked with indicia (4, 5, 6 and 7), dictating the order of removal of the protective liner pieces.

The support liner pieces 32L, 32R, 34L and 34R are peeled away from the external side 14 of the adhesive film from the center outwards. Each of the support liner pieces is designed as a generally straight segment, thereby reducing the tugging forces on the adhesive film 10 during removal of the support pieces. In addition, the shape and size of the support liner pieces 32L, 32R, 34L and 34R are designed such that the areas covered by each of these pieces are substantially similar so as not to create an imbalance in the tugging forces applied to the adhesive film 10.

Figure 1D:
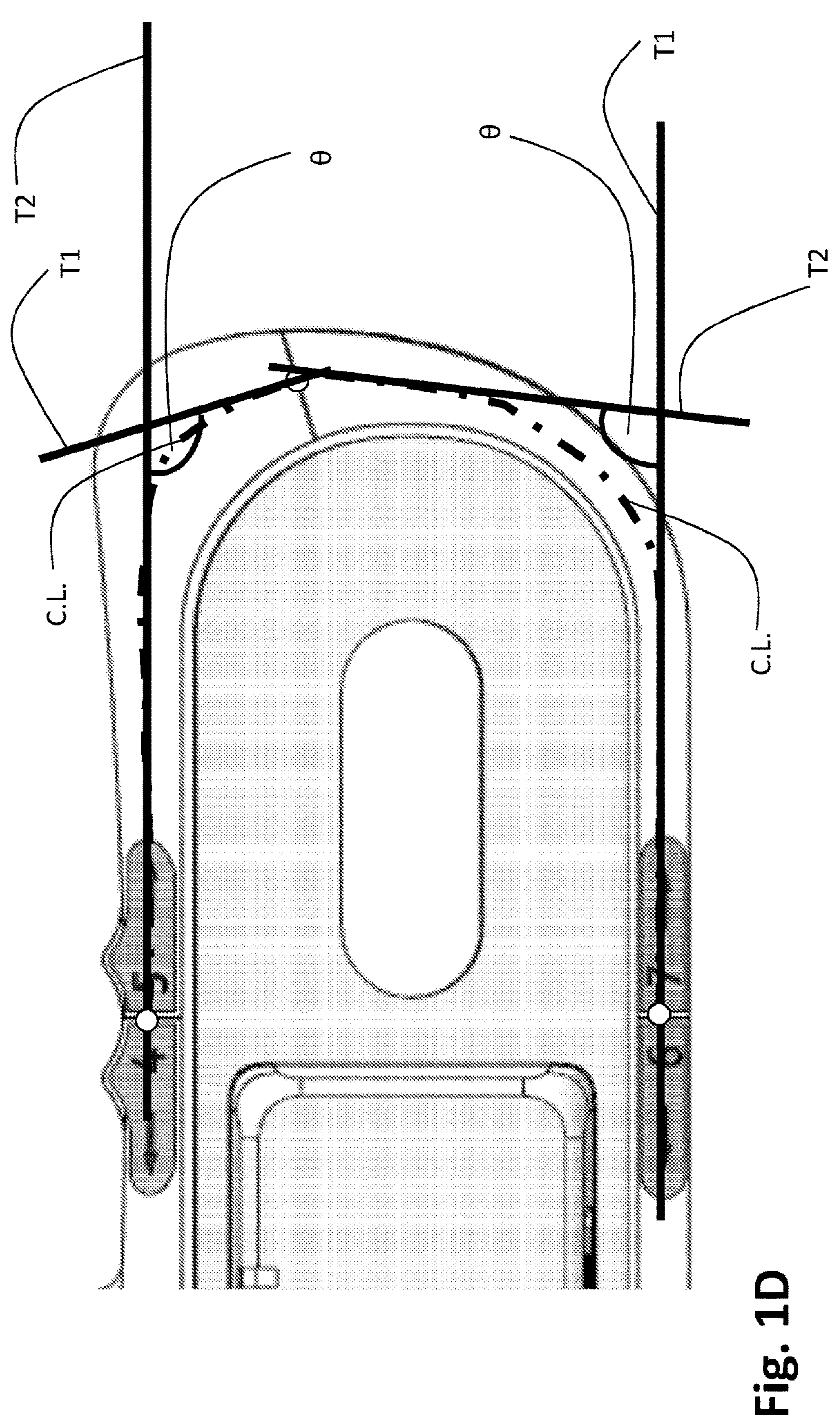
FIG. 1D is a schematic enlarged view of a side portion of the patch shown in FIG. 1.

With additional reference being made to FIG. 1D, each of the support liner pieces 32L, 32R, 34L and 34R extends along a centerline C.L. The shape and size of the support liner pieces is such that they do not extend over a certain angle θ along their trajectory. The angle θ is defined as the angle between two tangent lines T1 and T2, at lead and end points of the centerline C.L. Thus, the pulling back of the adhesive film 10 is prevented during removal of the support liner pieces. In other words, during removal of a support liner piece it is always pulled in essentially the same direction—outwards, without returning inwards (as would be the case if liner pieces 32R and 34R were a single piece). This design prevents unnecessary tugging forces on the adhesive film 10 which may otherwise have resulted in poorer adhesion, decreased functionality and lower placement accuracy.

After the support liner pieces 32L, 32R, 34L and 34R have been successfully peeled away, the patient or a health care practitioner (HCP) may further apply pressure with their fingers all along the periphery of the adhesive film 10 in order to secure the patch 1 to the patient's skin.

As noted before, the indicia on the protective liner pieces 22, 24 (1, 2 and 3), and on the support liner pieces 32L, 32R, 34L and 34R (4, 5, 6 and 7) help indicate to the HCP the order of removal/peeling of the pieces from the adhesive film 10.

Figure 2B:
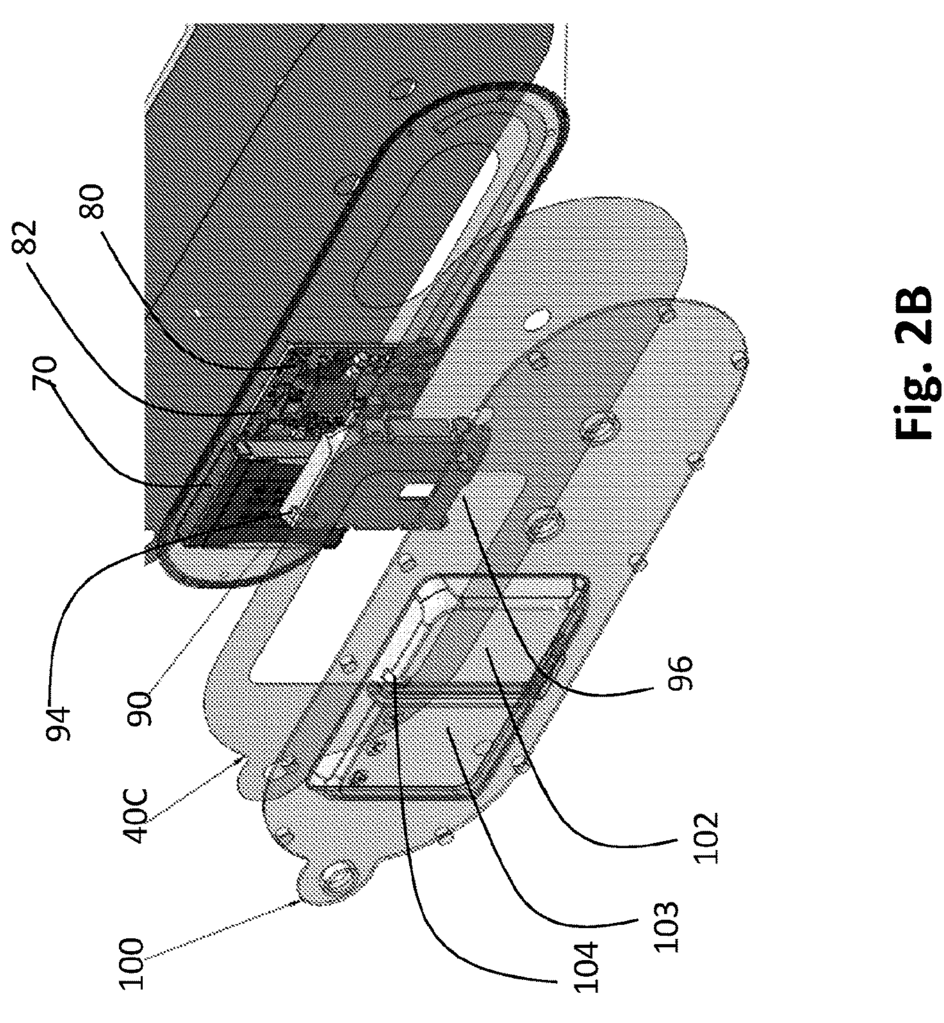
FIG. 2B is a schematic exploded isometric view of the communication layer shown in FIG. 2A.
Figure 2A:
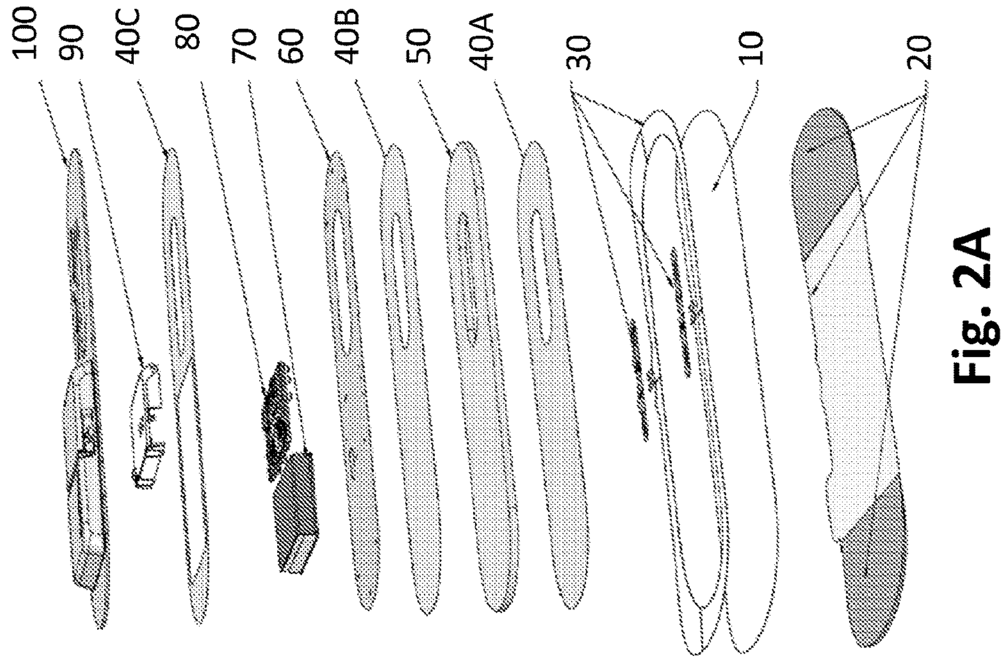
FIG. 2A is a schematic isometric exploded view of the patch shown in FIG. 1.

Attention is now drawn to FIG. 2, in which an exploded view of the patch 1 is shown, displaying the layer stack-up thereof. In particular, the patch 1 comprises:

- an adhesive film 10;
- a protective liner arrangement 20;
- a support liner arrangement 30;
- a first constructive adhesive layer 40A;
- a spacing layer 50;
- a second constructive adhesive layer 40B;
- a communication layer 60;
- a power unit 70;
- a processor unit 80;
- a cage 90; and
- a third constructive adhesive layer 40C and an external cover 100.

The spacing layer 50 is made of a material and having a thickness chosen to be such that minimally interferes with transmission and reception of signals between the communication layer and the in-vivo device. In addition, the material of the spacing layer is chosen to be such that returns to its original shape following deformation, thereby maintaining a fairly constant distance between the communication layer and the patient's skin (when the patch is applied). This distance insures proper communication between the communication layer and the in-vivo device. In accordance with a specific example, the spacing layer 50 is made of a closed-cell foam material.

In particular, the spacing layer 50 has a combination of three or more of the following features:

- low water retention (or low water absorption)—reducing the amount of water retained in the foam layer;
- puncture resistance—reducing the risk of accidental puncture of the medical patch by the user;
- differential stretchability—reducing the risk of tear of the medical patch;
- low breathability—reducing the chances of vapor reaching the functional components of the medical patch;
- good bond strength—increasing proper adhesion to the rest of the layers of the medical patch;
- low electric loss constant—reducing interference with communication; and
- high elastic recovery—increasing the chances of the medical patch properly withstanding stretching caused by movement and position of the patient.

One example of such a spacing layer 50, which may be used in the present invention is an EVA foam by 3M (3M EVA MSX-7373A).

It should also be noted here that most medical patches required breathability in order to better deal with sweating issues by the patient by allowing sweat to vaporize through the patch. However, in the present invention, such breathability proves disadvantageous, since such vapor may reach the communication layer and disrupt communication between the medical patch and the in-vivo device.

With additional reference being made to FIG. 2B, the communication layer 60 may be in the form of a flexible antenna, configured for both transmitting and receiving signals to and from the in-vivo device respectively. In particular, the communication layer 60 comprises a downlink antenna (not shown) configured for transmitting signals to the in-vivo device, and an uplink antenna (not shown) configured for receiving signals from the in-vivo device.

In addition, the communication layer may also be integrated with an adhesion detection arrangement 64 (not shown), configured for monitoring the adhesion state of the patch 1 to the patient's skin and provide an alert in case of detachment of the patch 1 from the skin. In accordance with a specific example, the adhesion detection arrangement may be constituted by a capacitance detection arrangement configured for measuring the electrical capacitance between the patch 1 and the patient's skin.

The processing unit 80 constitutes part of the communication layer 60, and is configured for transmitting signals to the downlink antenna and for receiving signals from the uplink antenna, processing signals and communicating with external devices (e.g. tablet, phone, PC, cloud etc.). The power unit 70 is connected to both the processing unit 80 and the communication layer 60 and is configured for providing power thereto.

In order to protect the communication layer, and specifically the power unit 70 and processing unit 80, there is provided an external cover layer 100, made of a flexible material. The cover layer 100 has two cavities 102, 103, configured for accommodating the power unit 70 and processing unit 80, protruding from the patch and received within these cavities. However, in order to further protect the processing unit 80 itself, there is provided a rigid cage 90 encapsulating the processing unit 80.

The processing unit 80 comprises an indication light 82 configured for alerting the patient on various actions and operation of the patch. In order for this indication light to be visible, the cage 90 comprises a transparent window 94 through which the indication light 82 is visible, and the cover layer 100 is formed with a cut out 104, through which the window 94 is visible.

In addition, the cage 90 further comprise an opening 96 configured for providing access to a USB port (not shown) of the processing unit 80. In accordance with a specific example, the opening may be provided with a flap that is naturally closed and may be torn open if access to the USB is required. Following tearing open, the flap may be closed again to cover the USB port.

The constructive adhesive layer 40A, 40B and 40C are used in order to adhere the various layers of the patch 1 to each other.

Figure 4A:
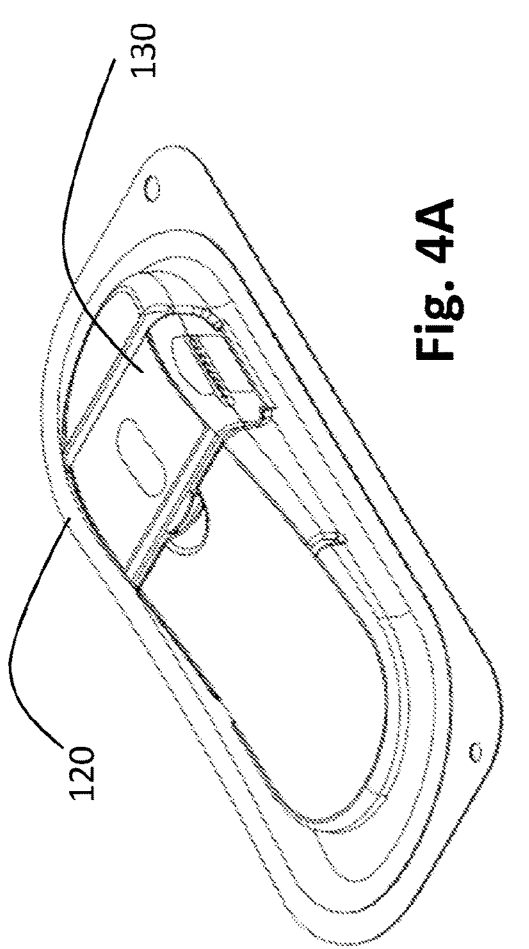
FIGS. 4A and 4B are schematic isometric and side views of a casing configured for housing the medical patch and an in-vivo device.
Figure 4B:
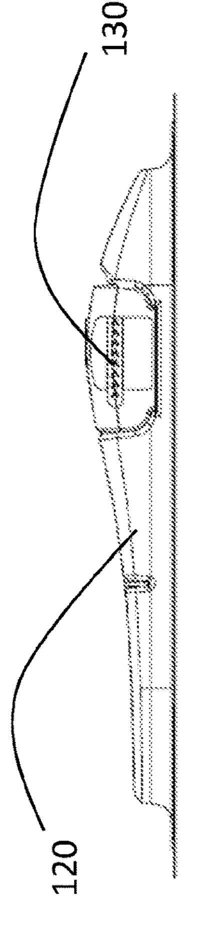

Attention is now drawn to FIGS. 4A and 4B, in which a casing 120 is shown, configured for accommodating therein the medical patch 1 and a swallowable in-vivo device (not shown). The casing 120 comprises a compartment 130 configured for accommodating the in-vivo device. The casing 120 also comprises a first magnetic safety arrangement (not shown) configured for preventing spontaneous operation of the medical patch 1, and the compartment 130 comprises a second magnetic safety arrangement (not shown) configured for preventing spontaneous operation of the in-vivo device.

When the casing is opened, and the medical patch 1 is removed therefrom, the first magnetic safety arrangement is no longer in proximity to the medical patch 1, thereby allowing turning it on. Similarly, when the in-vivo device is removed from the compartment 130, the second magnetic safety device is no longer in proximity to the in-vivo device, allowing it to function properly.

Those skilled in the art to which this invention pertains will readily appreciate that numerous changes, variations, and modifications can be made without departing from the scope of the invention, mutatis mutandis.

The invention claimed is:

1. A medical patch configured for being applied to skin of a patient and for communicating with an in-vivo device located within the patient's body, the medical patch comprising:

an adhesive film configured for adhering the patch to the skin of the patient, the adhesive film including a first side having an adhesive surface configured to be adhered to the skin of the patient and a second side opposite the first side;

a plurality of protective liners removably attached to the first side of the adhesive film and configured to cover the adhesive surface prior to application of the medical patch to the skin of the patient, the plurality of protective liners including:

a first protective liner removably attached to a first portion of the first side and configured to be removed from the adhesive film to expose the first portion for adhering the first portion to the skin of the patient; and at least one additional protective liner removably attached to a second portion of the first side adjacent to the first portion, the at least one additional protective liner configured to be removed, after adherence of the first portion to the skin of the patient, from the adhesive film to expose the second portion for adhering the second portion to the skin of the patient;

at least one support liner removably attached to the second side of the adhesive film and configured to structurally support the adhesive film during application of the medical patch to the skin of the patient;

an antenna configured for providing communication between the medical patch and the in-vivo device;

a spacing layer interposed between the adhesive film and the antenna;

a first double-sided adhesive layer interposed between the adhesive film and the spacing layer; and a second double-sided adhesive layer interposed between the antenna and the spacing layer.

2. The medical patch according to claim 1, wherein the antenna is configured to communicate with the in-vivo device during movement of the in-vivo device within the patient's body.

3. The medical patch according to claim 1, wherein the in-vivo device is a swallowable in-vivo device configured for traveling along at least a portion of the patient's GI tract.

4. The medical patch according to claim 1, wherein the adhesive film includes an inner surface and an outer surface, and the adhesive surface is disposed on at least a portion of the inner surface.

5. The medical patch according to claim 4, wherein the at least one protective liner is attached to the inner surface of the adhesive film and is configured for protecting the inner surface of the adhesive film prior to application of the medical patch to the skin of the patient.

6. The medical patch according to claim 1, wherein the at least one support liner comprises four support liners configured to be removed sequentially from the second side of the adhesive film after adherence of the adhesive surface to the skin of the patient, wherein the four support liners comprise two support liner pieces extending around a top edge of a peripheral region of the adhesive film, and two support liner pieces extending along a bottom curved edge of the peripheral region, and wherein the four support liners each has a turn angle smaller than 100 degrees.

7. The medical patch according to claim 1, wherein the at least one support liner comprises a plurality of support liners marked with indicia indicating a sequential order for removal of the plurality of support liners from the second side of the adhesive film after adherence of the adhesive surface to the skin of the patient.

8. The medical patch according to claim 1, wherein the spacing layer comprises closed-cell foam that returns to its original shape following deformation, thereby maintaining separation between the antenna and the patient.

9. The medical patch according to claim 1, wherein each protective liner of the plurality of protective liners is marked with indicia indicating a sequential order for removal of the plurality of protective liners from the first side of the adhesive film during application of the medical patch to the skin of the patient.

10. The medical patch according to claim 1, wherein the first protective liner is removably attached to a middle portion of the first side and the at least one additional protective liner comprises:

a second protective liner removably attached to a first end portion of the first side, the first end portion being adjacent to a first end of the middle portion; and a third protective liner removably attached to a second end portion of the adhesive film layer, the second end portion being adjacent to a second end of the middle portion such that the first and second end portions are separated by the middle portion, wherein:

the first protective liner is configured to be removed from the adhesive film layer prior to the second and third protective liners to expose the middle portion and adhere the middle portion to the skin of the patient prior to removal of the second and third protective liners; and the second and third protective liners are configured to be sequentially removed from the adhesive film layer after adherence of the middle portion to the skin of the patient to expose the respective first and second end portions and adhere the first and second end portions to the skin of the patient.

11. A method for applying a medical patch to skin of a patient, the method comprising:

removing a first protective liner from a first side of an adhesive layer of the medical patch to expose a first portion of the first side of the adhesive layer;

adhering the first portion of the first side of the adhesive layer to the skin of the patient;

removing, after removing of the first protective liner and after adhering of the first portion to the skin of the patient, at least one additional protective liner from the first side of the adhesive layer to expose a second portion of the first side adjacent to the first portion;

adhering the second portion to the skin of the patient;

removing, after removing of the at least one additional protective liner and after adhering of the second portion to the skin of the patient, a support liner from a second side of the adhesive layer, the second side of the adhesive layer being opposite the first side of the adhesive layer; and removing, after removing of the support liner, at least one additional support liner from the second side of the adhesive layer, wherein the medical patch includes a spacing layer interposed between the adhesive layer and an antenna, a first double-sided adhesive layer interposed between the adhesive layer and the spacing layer, and a second double-sided adhesive layer interposed between the antenna and the spacing layer.

12. The method according to claim 11, wherein removing the support liner from the second side of the adhesive layer includes removing the support liner from an outer periphery area of the adhesive layer.

13. The method according to claim 11, wherein removing the first protective liner and removing the at least one additional protective liner includes removing a plurality of protective liners sequentially in accordance with indicia included on the plurality of protective liners, the indicia indicating a sequential order for removing of the plurality of protective liners.

14. The method according to claim 11, wherein removing the support liner and removing the at least one additional support liner includes removing a plurality of support liners sequentially in accordance with indicia included on the plurality of support liners, the indicia indicating a sequential order for removing of the plurality of support liners subsequent to the removing of the at least one additional protective liner.

15. The method according to claim 11, wherein:

removing the first protective liner includes removing the first protective liner from a middle portion of the first side and adhering the middle portion to the skin of the patient; and removing the at least one additional protective liner includes:

removing, after adhering of the middle portion to the skin of the patient, a second protective liner from a first end portion of the first side, the first end portion being adjacent to a first end of the middle portion;

adhering the first end portion to the skin of the patient;

removing, after adhering the first end portion to the skin of the patient, a third protective liner from a second end portion of the first side, the second end portion being adjacent to a second end of the middle portion; and adhering the second end portion to the skin of the patient.

16. A medical patch configured for being applied to skin of a patient and for communicating with an in-vivo device located within the patient's body, the medical patch comprising:

a communication layer comprising an antenna configured for providing communication between at least one of the in-vivo device and the medical patch or the medical patch and an external device;

an adhesive film layer configured for adhering the medical patch to the skin of the patient;

a plurality of protective liners removably attached to the adhesive film layer, the plurality of protective liners including:

a first protective liner removably attached to a first portion of the adhesive film layer and configured to be removed from the adhesive film layer to expose the first portion for adhering the first portion to the skin of the patient; and at least one additional protective liner removably attached to a second portion of the adhesive film layer adjacent to the first portion, the at least one additional protective liner configured to be removed from the adhesive film layer after adherence of the first portion to the skin of the patient to expose the second portion for adhering the second portion to the skin of the patient;

a spacing layer interposed between the adhesive film layer and the communication layer for separating the communication layer of the medical patch from the skin of the patient such that the communication layer is not in direct contact with the skin of the patient;

a first double-sided adhesive layer interposed between the adhesive film layer and the spacing layer and configured to attach the adhesive film layer to the spacing layer; and a second double-sided adhesive film layer interposed between the communication layer and the spacing layer and configured to attach the communication layer to the spacing layer.

17. The medical patch according to claim 16, wherein the first protective liner is removably attached to a middle portion of the adhesive film layer and the at least one additional protective liner comprises:

a second protective liner removably attached to a first end portion of the adhesive film layer, the first end portion being adjacent to a first end of the middle portion; and a third protective liner removably attached to a second end portion of the adhesive film layer, the second end portion being adjacent to a second end of the middle portion such that the first and second end portions are separated by the middle portion, wherein:

the first protective liner is configured to be removed from the adhesive film layer prior to the second and third protective layers to expose the middle portion and adhere the middle portion to the skin of the patient prior to removal of the second and third protective liners; and the second and third protective liners are configured to be sequentially removed from the adhesive film layer after adherence of the middle portion to the skin of the patient to expose the respective first and second end portions and adhere the first and second end portions to the skin of the patient.

* * * * *